(12) United States Patent
Levin

(10) Patent No.: US 11,823,356 B2
(45) Date of Patent: *Nov. 21, 2023

(54) SYSTEMS AND METHODS INCLUDING MOTION COMPENSATION IN A THREE-DIMENSIONAL SCAN

(71) Applicant: Align Technology, Inc., San Jose, CA (US)

(72) Inventor: Adi Levin, Nes Tziona (IL)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/696,815

(22) Filed: Mar. 16, 2022

(65) Prior Publication Data

US 2022/0207660 A1 Jun. 30, 2022

Related U.S. Application Data

(63) Continuation of application No. 16/808,298, filed on Mar. 3, 2020, now Pat. No. 11,321,817, which is a
(Continued)

(51) Int. Cl.
*G06T 5/00* (2006.01)
*A61C 9/00* (2006.01)
(Continued)

(52) U.S. Cl.
CPC ................ *G06T 5/003* (2013.01); *A61B 1/24* (2013.01); *A61B 6/145* (2013.01); *A61C 9/0053* (2013.01); *A61C 9/0066* (2013.01); *G06T 5/006* (2013.01); *G06T 7/20* (2013.01); *G06T 7/38* (2017.01); *G06T 2207/10028* (2013.01);
(Continued)

(58) Field of Classification Search
CPC ........... G06T 5/003; G06T 7/38; G06T 5/006; G06T 7/20; G06T 2207/20048; G06T 2207/10028; G06T 2207/20201; G06T 2207/30241; G06T 2207/30036;
(Continued)

(56) References Cited

U.S. PATENT DOCUMENTS 8,948,482 B2 2/2015 Levin
D925,739 S 7/2021 Shalev et al.
(Continued)

*Primary Examiner* — Ali Bayat
(74) *Attorney, Agent, or Firm* — Shay Glenn LLP

(57) ABSTRACT

The present disclosure provides computing device implemented methods, computing device readable media, and systems for motion compensation in a three dimensional scan. Motion compensation can include receiving three-dimensional (3D) scans of a dentition, estimating a motion trajectory from one scan to another, and calculating a corrected scan by compensating for the motion trajectory. Estimating the motion trajectory can include one or more of: registering a scan to another scan and determining whether an amount of movement between the scans is within a registration threshold; determining an optical flow based on local motion between consecutive two-dimensional (2D) images taken during the scan, estimating and improving a motion trajectory of a point in the scan using the optical flow; and estimating an amount of motion of a 3D scanner during the scan as a rigid body transformation based on input from a position tracking device.

21 Claims, 6 Drawing Sheets

Related U.S. Application Data continuation of application No. 16/389,323, filed on Apr. 19, 2019, now Pat. No. 10,600,160, which is a continuation of application No. 15/730,492, filed on Oct. 11, 2017, now Pat. No. 10,275,862, which is a continuation of application No. 15/421,110, filed on Jan. 31, 2017, now Pat. No. 9,830,688, which is a continuation of application No. 14/970,030, filed on Dec. 15, 2015, now Pat. No. 9,589,329, which is a continuation of application No. 14/578,233, filed on Dec. 19, 2014, now Pat. No. 9,214,014, which is a continuation of application No. 13/666,812, filed on Nov. 1, 2012, now Pat. No. 8,948,482.

(51) Int. Cl.
*G06T 7/20* (2017.01)
*A61B 1/24* (2006.01)
*A61B 6/14* (2006.01)
*G06T 7/38* (2017.01)

(52) U.S. Cl.
CPC ............... *G06T 2207/20048* (2013.01); *G06T 2207/20201* (2013.01); *G06T 2207/30036* (2013.01); *G06T 2207/30241* (2013.01)

(58) Field of Classification Search
CPC ......... A61B 1/24; A61B 6/145; A61C 9/0053; A61C 9/0066
USPC .......................................................... 382/107
See application file for complete search history.

(56) References Cited

U.S. PATENT DOCUMENTS

| | | | |
|---|---|---|---|
| 2007/0171220 A1* | 7/2007 | Kriveshko | G06T 7/30 345/419 |
| 2007/0172112 A1* | 7/2007 | Paley | G06T 1/0007 382/128 |
| 2008/0015727 A1* | 1/2008 | Dunne | B33Y 30/00 700/118 |
| 2011/0050848 A1* | 3/2011 | Rohaly | G06T 15/10 348/43 |
| 2011/0176723 A1* | 7/2011 | Ali | G06T 7/246 382/154 |
| 2021/0121049 A1 | 4/2021 | Rudnitsky et al. | |
| 2021/0128281 A1 | 5/2021 | Peleg | |
| 2021/0137653 A1 | 5/2021 | Saphier et al. | |
| 2021/0196152 A1 | 7/2021 | Saphier et al. | |

* cited by examiner

SYSTEMS AND METHODS INCLUDING MOTION COMPENSATION IN A THREE-DIMENSIONAL SCAN

CROSS REFERENCE TO RELATED APPLICATIONS

This application is a continuation of U.S. patent application Ser. No. 16/808,298, filed Mar. 3, 2020, now U.S. Patent Application Publication No. 2020/0202497, which is a continuation of U.S. patent application Ser. No. 16/389,323, filed Apr. 19, 2019, now U.S. Pat. No. 10,600,160, which is a continuation of U.S. patent application Ser. No. 15/730,492, filed Oct. 11, 2017, now U.S. Pat. No. 10,275,862, which is a continuation of U.S. patent application Ser. No. 15/421,110, filed Jan. 31, 2017, now U.S. Pat. No. 9,830,688, which is a continuation of U.S. patent application Ser. No. 14/970,030, filed Dec. 15, 2015, now U.S. Pat. No. 9,589,329, which is a continuation of U.S. patent application Ser. No. 14/578,233, filed Dec. 19, 2014, now U.S. Pat. No. 9,214,014, which is a continuation of U.S. patent application Ser. No. 13/666,812, filed Nov. 1, 2012, now U.S. Pat. No. 8,948,482, each of which is incorporated by reference in its entirety herein.

BACKGROUND

The present disclosure is related generally to the field of dental treatment. More particularly, the present disclosure is related to methods, devices, and systems for motion compensation in a three dimensional scan.

Dental treatments may involve, for instance, restorative and/or orthodontic procedures. Restorative procedures may be designed to implant a dental prosthesis (e.g., a crown, bridge inlay, onlay, veneer, etc.) intraorally in a patient. Orthodontic procedures may include repositioning misaligned teeth and changing bite configurations for improved cosmetic appearance and/or dental function. Orthodontic repositioning can be accomplished, for example, by applying controlled forces to one or more teeth over a period of time.

As an example, orthodontic repositioning may be provided through a dental process that uses positioning appliances for realigning teeth. Such appliances may utilize a thin shell of material having resilient properties, referred to as an "aligner," that generally conforms to a patient's teeth but is slightly out of alignment with a current tooth configuration.

Placement of such an appliance over the teeth may provide controlled forces in specific locations to gradually move the teeth into a new configuration. Repetition of this process with successive appliances in progressive configurations can move the teeth through a series of intermediate arrangements to a final desired arrangement.

Such systems typically utilize materials that are light weight and/or transparent to provide as a set of appliances that can be used serially such that as the teeth move, a new appliance can be implemented to further move the teeth.

A scanning system may be used to obtain digital data representing a patient's teeth in their current position (i.e., at the time of the scan), which will be considered herein as an initial digital data set (IDDS) representing an initial tooth arrangement. The IDDS may be obtained in a variety of ways. This can be used for dental records or treatment purposes.

For example, the patient's teeth may be imaged directly or indirectly (e.g., through the use of a model or impression) to obtain digital data using direct and/or indirect structured light, X-rays, three-dimensional X-rays, lasers, destructive scanning, computing device-aided tomographic images or data sets, magnetic resonance images, intra-oral scanning technology, photographic reconstruction, and/or other imaging techniques. The IDDS can include an entire mouth tooth arrangement, some, but not all teeth in the mouth, and/or it can include a single tooth.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
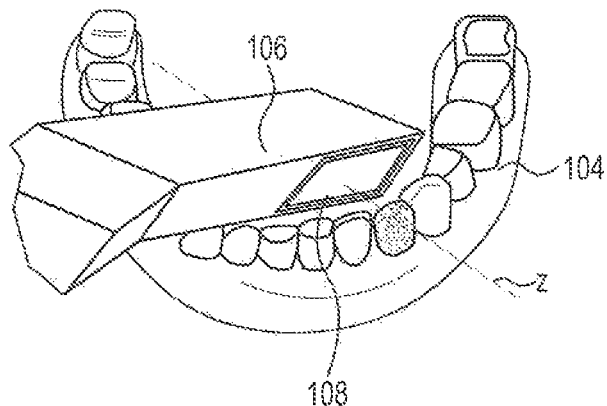
FIGS. 1A-1B illustrate alternate perspective views of an intraoral scanner according to a number of embodiments of the present disclosure.

A positive model and/or negative impression of the patient's teeth or a tooth may be scanned, for example, using an X-ray, laser scanner, destructive scanner, structured light, and/or other range acquisition system to produce the IDDS. The data set produced by the range acquisition system may be converted to other formats to be compatible with the software which is used for manipulating images within the data set, as described herein.

Whether scanning a patient's dentition directly, or scanning a model or impression of the patent's dentition, it may be desirable to support scanning while the scanner is moving with respect to the teeth. Such support can be beneficial for both video scanning (e.g., a continuous sequence of images) and point-and-shoot scanning (e.g., a number of discrete images).

With point-and-shoot scanning, a user can trigger the scan. After the scan is triggered, a fast scan can be beneficial to reduce distortion in the scan that may be caused by motion of the scanner that might otherwise occur during a slow scan (e.g., during a time between initiation and completion of the scan). It may be reasonable to assume that movements associated with point-and-shoot scanning are relatively small (e.g., as compared to movements during video scanning) because the user is trying to keep the scanner stable (e.g., as opposed to moving during video scanning).

A slow scan can result in large movements of the scanner with respect to the object during the scan, which can result in motion in the results of the scan (e.g., motion blur). As used herein, a slow scan does not indicate a long exposure during a scan. Rather, a slow scan can indicate that a relatively long period of time is used to take multiple single images in the course of a single 3D scan. Thus, it can take a relatively long time (e.g., 250-400 milliseconds (msec)) to capture a 3D scan. Each image on its own may or may not suffer motion blur. However, the effect of motion over the course of scans comprising the 3D scan can be that the relative position between raw images is unknown, thus causing geometric distortion (e.g., due to interpretation of the raw images, which may assume a certain relative position between the images). However, a faster scan (e.g., 50 msec) can be more difficult to accomplish (e.g., may call for more expensive and/or advanced hardware and/or may call for more and/or faster computation capabilities versus a slower scan). Unless otherwise noted, the term scan, as used herein, can refer to either or both of video and point-and-shoot scanning.

With continuous scanning, a scanner can automatically take a particular number of scans over a particular amount of time (e.g., x-number of scans per second). It may be reasonable to assume a scanner velocity of approximately five millimeters (mm) per second (sec). However, even with a fast scan of 50 msec, this can still include a scanner drift of 250 microns in some implementations. Thus, motion compensation can be beneficial even for video scanning with fast scans.

As used herein, motion detection refers to a determination whether a scanner moved significantly with respect to the object. In some embodiments, scans with detected motion can be rejected. As used herein, motion compensation refers to correction for distortions in a scan caused by motion of the scanner. An example of motion compensation can include an estimation of a spatial trajectory of the scanner (e.g., how the scanner moves in space) as a function of time in the duration of each single scan (e.g., as a function of time for each scan). Such information can be used to compensate for distortions in a scan. In some embodiments, the result of a 3D scan can be a point cloud that represents the scanned object (e.g., patient's dentition). Motion compensation can be applied to the point cloud to correct for any distortions resulting from the scan.

Some difficulties that may arise with motion compensation include complex motion (e.g., the scanner may move with six degrees of freedom and/or with an unsteady velocity). This may be particularly true for hand-held scanners that may contact the patient's teeth where friction and/or collisions can cause a sudden acceleration. Other difficulties include the patient's jaws moving during a scan. Some embodiments of the present disclosure include the use of position tracking devices in the scanner (e.g., an accelerometer and/or a gyroscope, among other inertial devices, wireless devices, or other devices) to help measure movements of the scanner, but such devices cannot account for movement of the patient's jaws. Another difficulty can include motion of the soft tissue (e.g., tongue, lips, cheek) of the patient, which may confuse some optical methods for computing motion of the scanner relative to the teeth.

The present disclosure provides computing device implemented methods, computing device readable media, and systems for motion compensation in a three dimensional scan. Motion compensation can include receiving three-dimensional (3D) scans of a dentition, estimating a motion trajectory from one scan to another, and calculating a corrected scan by compensating for the motion trajectory. Estimating the motion trajectory can include one or more of: registering a scan to another scan and determining whether an amount of movement between the scans is within a registration threshold; determining an optical flow based on local motion between consecutive two-dimensional (2D) images taken during the scan, estimating and improving a motion trajectory of a point in the scan using the optical flow; and estimating an amount of motion of a 3D scanner during the scan as a rigid body transformation based on input from a position tracking device In some embodiments, motion compensation can include receiving first data from a 3D scan of a dentition taken with a 3D scanner in a first reference frame and receiving second data from two-dimensional (2D) images of the dentition taken during the 3D scan of the dentition with a 2D imager in a second reference frame that is fixed with respect to the first reference frame, where each of the 2D images is associated with a respective time in the 3D scan. Motion compensation can include determining an optical flow based on local motion between consecutive images of the 2D images, estimating a motion trajectory of a point in the 3D scan, and improving the estimated motion trajectory using the optical flow to estimate a correctness of the estimated motion trajectory. Motion can be compensated for during the 3D scan using the improved estimated motion trajectory.

In a number of embodiments, a system for motion compensation can include a scanning module including an intraoral 3D scanner and at least one position tracking device coupled to the 3D scanner. The system can also include a processing module coupled to the scanning module to estimate an amount of motion of the 3D scanner during a 3D scan as a rigid body transformation based on input from the at least one position tracking device and compensate for the amount of motion by applying an inverse of the rigid body transformation to a plurality of points comprising the 3D scan.

In the detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure. As used herein, the designator "N", particularly with respect to reference numerals in the drawings, indicates that a number of the particular feature so designated can be included. As used herein, "a number of" a particular thing can refer to one or more of such things (e.g., a number of teeth can refer to one or more teeth).

The figures herein follow a numbering convention in which the first digit or digits correspond to the drawing figure number and the remaining digits identify an element or component in the drawing. Similar elements or components between different figures may be identified by the use of similar digits. For example, 104 may reference element "04" in FIG. 1, and a similar element may be referenced as 204 in FIG. 2. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention, and should not be taken in a limiting sense.

Figure 1B:
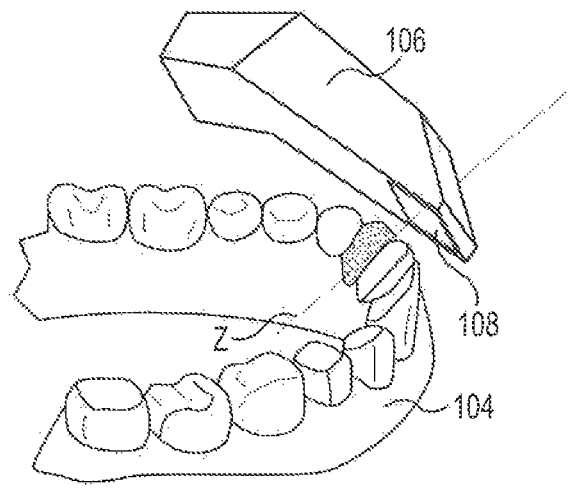

FIGS. 1A-1B illustrate alternate perspective views of an intraoral scanner according to a number of embodiments of the present disclosure. The spatial relationship of the scanner 106 with respect to the dentition 104 in the intraoral cavity is shown. A plurality of images showing the relationship at any other desired vantage point (viewpoint) may be provided on a display.

Images presented on a display to a user can be composites of virtual models of the dentition 104 ac created with aid of the scanner 106 and stored in memory (see, for example, FIG. 7). These virtual models can be manipulated by the user and/or the computing device to provide the correct spatial relationship, in virtual space and can be displayed as 2D or 3D images. Optionally, the position of the scanner 106 and the direction of the scanning axis (e.g., z-axis) can be displayed with respect to the dentition 104. The scanning axis (e.g., z-axis) can be defined as orthogonal to the scanning face 108 of the scanner 106, but may be defined according to other suitable geometric or other parameters of the scanner 106. The images of the dentition 104 can be displayed as having 3D attributes and realistic dental morphologies and/or each dental surface can be represented, for example, by a geometrical form (e.g., simple wedges representing incisors, cones representing canines, and cylinders representing molars).

The virtual model can be custom-modified to show a virtual preparation at each corresponding dental site where a real preparation is to be found. Virtual teeth may be removed from the model where none are to be found in the real intraoral cavity (e.g., where real teeth have been removed subsequent to obtaining the IDDS). These features can further facilitate identification of the positions and orientations of the scanner 106 with respect to the dentition 104.

Figure 2:
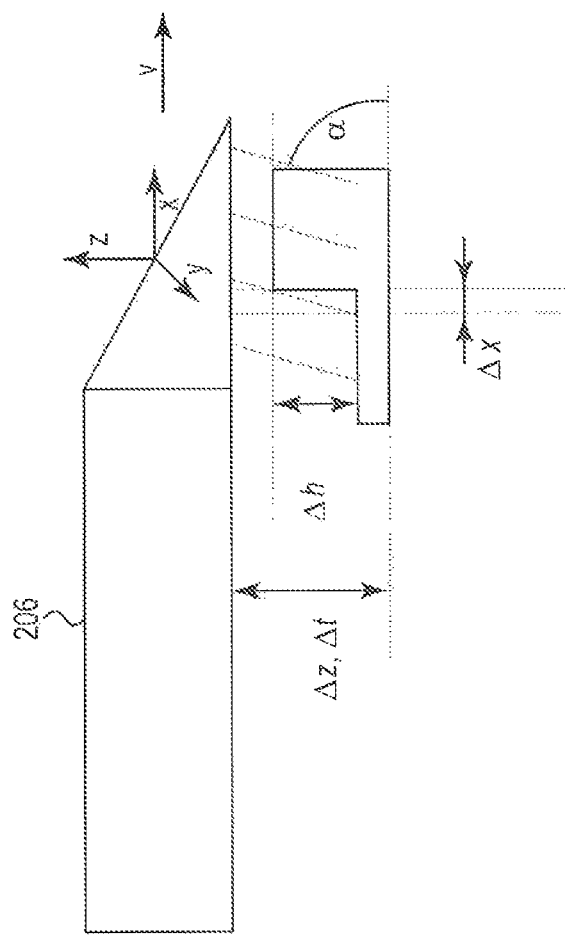
FIG. 2 is a diagram illustrating motion of a scanner relative to an object being scanned according to a number of embodiments of the present disclosure.

FIG. 2 is a diagram illustrating motion of a scanner 206 relative to an object 210 being scanned according to a number of embodiments of the present disclosure. The result of scanning (e.g., after some processing of the scanned data) is a collection of points (x,y,z,t), where t is a time of focus and x, y, and z are 3D coordinates with respect to the coordinate system of the scanner 206 at time t. Data that might otherwise be captured by a scanner 206 may be lost due to motion drift of the scanner 206 during scanning. For example, walls above a certain angle may be invisible to the scanner 206 and/or areas near vertical walls may be invisible.

Assuming a constant lateral speed (v) of the scanner 206 and assuming a constant speed of scanning, $$\tan\alpha = \frac{\Delta z}{v \Delta t},$$

where α is the drift angle (e.g., in degrees), Δz is the distance between the scanner 206 and the object 210 (e.g., in mm), v is the velocity of the scanner 206 (e.g., in mm/sec), and Δt is the duration of the scan (e.g., in msec). The following table includes some example drift angles for Δz=15 mm.

TABLE 1

| | α (degrees) | |
|---|---|---|
| Δt (msec) | v = 5.0 mm/sec | V = 10.0 mm/sec |
| 50 | 89 | 88 |
| 100 | 88 | 86 |
| 150 | 87 | 84 |
| 200 | 86 | 82 |
| 250 | 85 | 80 |

Missing data (e.g., due to the drift angle described above) can be defined as $$\Delta x = \frac{\Delta h}{\tan\alpha} = v \frac{\Delta h \Delta t}{\Delta z},$$

where Δx is the width of the missing portion (e.g., in microns) and Δh is the height of the missing portion (e.g., in mm). The following table includes some example of amounts of missing data for Δz=15 mm and Δh=10 mm.

TABLE 2

| | Δx (microns) | |
|---|---|---|
| Δt (msec) | v = 5.0 mm/sec | V = 10.0 mm/sec |
| 50 | 166 | 333 |
| 100 | 333 | 666 |
| 150 | 500 | 1000 |
| 200 | 666 | 1333 |
| 250 | 833 | 1666 |

Because of imperfections in scanning technique and assuming general ray geometry, the scan may not have telecentric properties (e.g., having rays entering the scanner 206 parallel to the z-axis), the focal surface is not necessarily a plane (e.g., a flat surface may appear curved and/or a non-flat object 210 represented in the image as a focal surface may not be represented in a plane as it might otherwise), and the scan may include arbitrary scanning patterns (e.g., the z-axis may not be consistent with respect to the object during the scan, that is, the scanner 206 may not be consistently pointed directly at the object 210 during the scan). This can result in a distorted image that appears to bow and/or curve where it shouldn't, among other distortions. For example, a rectangle might appear as a parallelogram, perhaps with curved sides.

According to various embodiments of the present disclosure, motion estimation can include any one of, or any combination of approximation based on registration results, image processing with optical flow, the use of position tracking devices with the scanner 206, differential signaling between the scanner 206 and a plurality of wireless transmitters, and/or the use of any other motion estimation/position tracking technique. Use of registration results can measure motion relative to the teeth, is relatively easy to compute, and is generally not confused by soft tissue, but may have inaccuracies due to assumption of a simplified motion trajectory and may have performance limited based on a scanning rate. Use of image processing with optical flow can measure motion relative to the teeth and can have relatively high accuracy, but may be computationally intensive and may be confused by soft tissues. Use of position tracking devices is relatively easy to compute but may be confused by gravitation and may be indifferent to patient movements.

Figure 3:
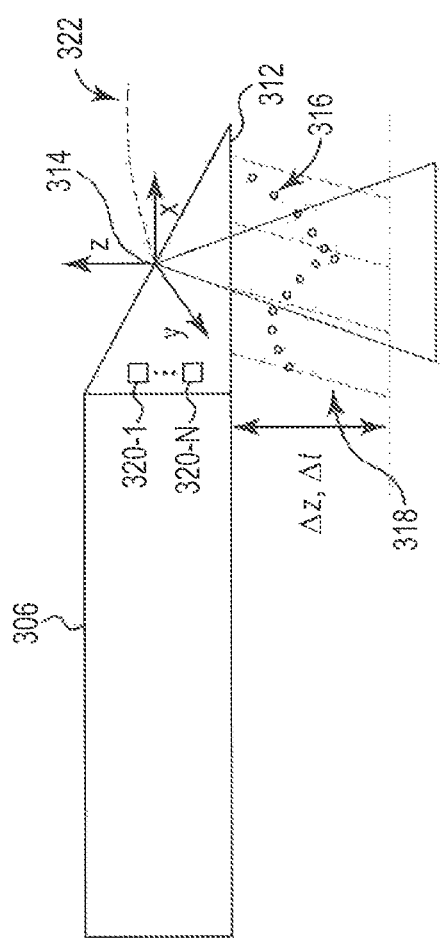
FIG. 3 is a diagram illustrating a scanner according to a number of embodiments of the present disclosure.

FIG. 3 is a diagram illustrating a scanner 306 according to a number of embodiments of the present disclosure. For example, the scanner 306 can be a hand-held intraoral scanner. The scanner 306 can include a 3D scanner 312. By way of example, the 3D scanner 312 can determine a 3D structure by confocal focusing of an array of light beams, as will be appreciated by those of ordinary skill in the art. The scanner 306 can include only a 3D scanner 312, or a 3D scanner 312 in combination with one or more of a 2D imager 314 and a number of position tracking devices 320-1, . . .

320-N. The position tracking devices 320-1, ..., 320-N can include, for example, an accelerometer (e.g., to measure acceleration of the scanner 306) and a gyroscope (e.g., to measure angular velocity of the scanner 306), among others. Although not specifically illustrated, the scanner 306 can include and or be coupled to a computing device (e.g., including a processor and memory as is illustrated in FIG. 7).

The 2D imager 314 can be analogous to a digital camera. The 2D imager 314 can be configured to continuously capture discrete images of the object while the 3D scanner 312 is scanning the object. The 2D imager 312 can be fixed with respect to the 3D scanner 312 such that any movement of the scanner 306 equally affects the 2D imager 312 and the 3D scanner 312 (e.g., reference frame of the 2D imager 312 can be fixed with respect to a reference frame of the 3D scanner). Furthermore, the 2D imager 312 can be non-concentric with respect to the 3D scanner 312 (e.g., to improve sensitivity to motion along the z-axis).

As is illustrated in FIG. 3, the position of a focal point of a single beam of light 318 from the 3D scanner 312 is not vertical because the scanner 306 is moving during the scan. The scanner 306 can move along a trajectory 322 such that the scanner 306, during a time of capture of the 3D scan (e.g., $\Delta t$) the focal plane can move a particular distance (e.g., $\Delta z$). The result of 3D scanning (e.g., after some processing of the scanned data) can be a collection of points 316. In some instances, reconstruction of the trajectory 322 can be limited to a constant-speed trajectory.

In some embodiments, motion of the 3D scanner 312 can be tracked based only on input from the position tracking devices 320-1, ..., 320-N and input from the 2D imager 314 (e.g., without using input from the 3D scanner 312). Such motion tracking may be based on an assumption that the patient's jaw doesn't change its orientation. The position tracking devices 320-1, ..., 320-N can provide information indicating a change in orientation of the 3D scanner 312 (e.g., in three degrees of freedom). The analysis of 2D images can provide information indicating a change in orientation in the other three degrees of freedom.

In various embodiments, a velocity of the 3D scanner 312 can be estimated based on input from the position tracking devices 320-1, ..., 320-N. The estimated velocity can be reset to zero in response to input from the 2D imager 314 indicating that the 3D scanner 312 is not moving. For example, the estimated velocity can be reset to zero in six degrees of freedom in response to the input from the 2D imager 314 comprising a plurality of 2D images indicating that the 3D scanner 312 is not moving. Such embodiments can be beneficial in avoiding large error drifts. If the user keeps the scanner 306 stable from time to time, the 2D images can be used to determine when the scanner 306 is held in the stable position.

Figure 4:
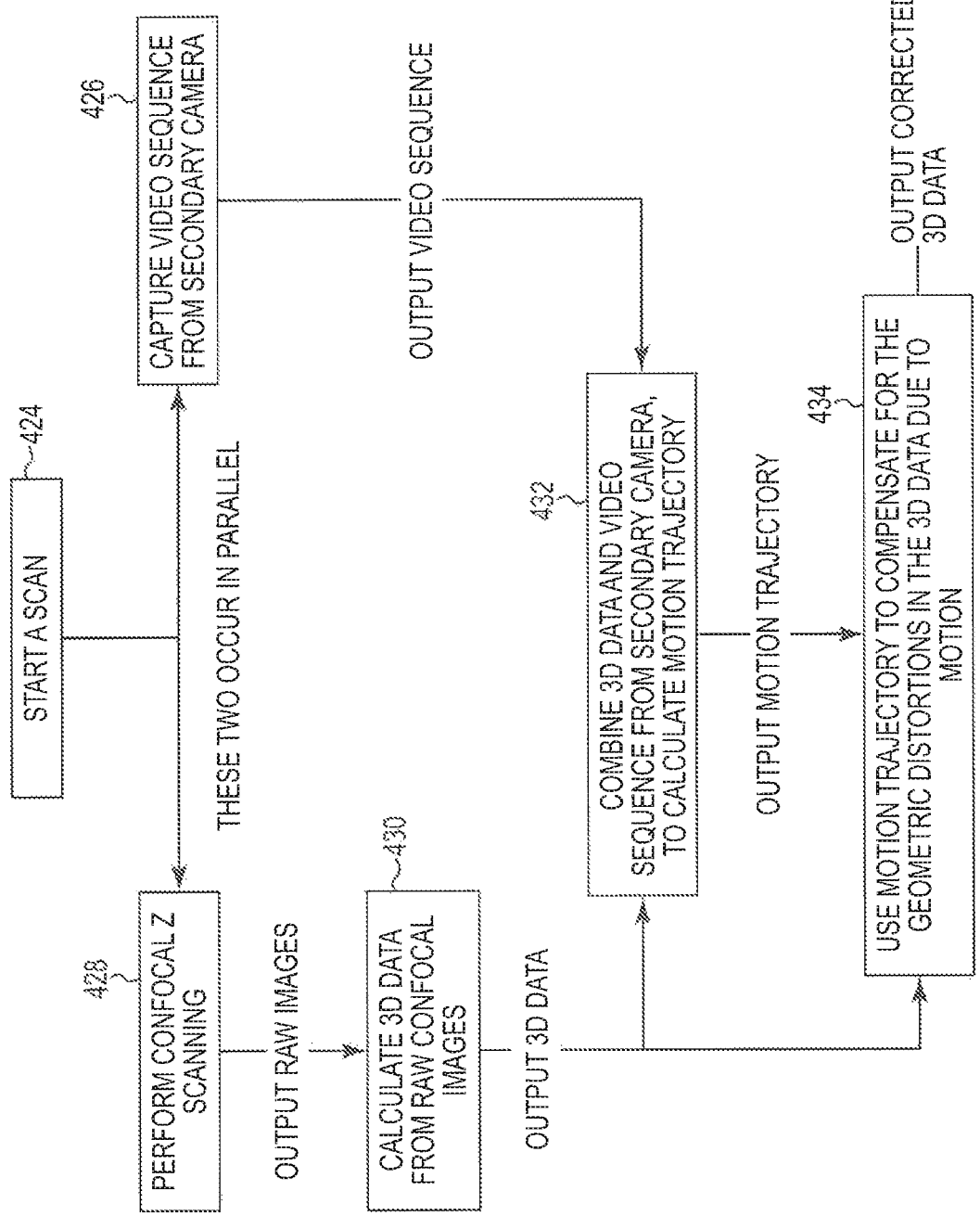
FIG. 4 is a flow chart illustrating a method for motion compensation using 3D and 2D data according to a number of embodiments of the present disclosure.

FIG. 4 is a flow chart illustrating a method for motion compensation using 3D and 2D data according to a number of embodiments of the present disclosure. A scan 424 can be initiated. A first input to an image processing algorithm can be data from a 3D scan 428 (e.g., a height map that is a result of some initial processing of data gathered by the 3D scanner) of a dentition taken with the 3D scanner in a first reference frame. In some embodiments, the 3D data can result from a confocal scan in the z-direction.

A second input to the image processing algorithm can be a plurality of 2D images 426 of the dentition (e.g., a video sequence) taken during the 3D scan of the dentition with a 2D imager (e.g., a secondary camera) in a second reference frame that is fixed with respect to the first reference frame.

In some embodiments, the 2D imager can have a high depth of field, which can help provide identical or nearly identical quality of motion estimation throughout the entire depth of scanning. In some embodiments, the second reference frame can be non-telecentric for improved sensitivity to motion along the z-axis. Each of the 2D images can be associated with a respective time in the 3D scan (e.g., each of the 2D images can be captured and time stamped in the duration of the 3D scan).

In some embodiments, an heuristic can be used to determine which points in the 3D scan are visible in a particular one of the plurality of 2D images (e.g., prior to determining an optical flow). If a 3D point is occluded at a certain time, then checking the optical flow along its path could lead to inaccurate results. Accordingly, 3D points that are occluded and/or that go out of the field-of-view in each 2D image can be filtered out from the analysis.

The result of 3D scanning 430 (e.g., after some processing of the scanned data) can be a collection of points (x, y, z, t), where t is a time of focus and x, y, and z are 3D coordinates with respect to the coordinate system of the 3D scanner at time t. A 2D image can include a number of pixels with coordinates (i, j, t), where i and j are coordinates of the pixel on a sensor of the 2D imager and t corresponds to a time in the 3D scan that the 2D image was taken. The coordinates x, y, and z can be calculated from (i, j, t) where i and j are indices of a pixel on a sensor of the scanner. In some embodiments, the mapping from (i, j, t) to (x, y, z) can be a constant map from 3D to 3D that takes into consideration constant geometrical distortions, but assumed that the scanner is not moving. A point (x, y, z) in the coordinate system of the 3D scanner can be mapped to pixel coordinates (i, j) of the 2D imager. The time (t) is not necessarily proportional to z as in confocal systems. For example, a scan can be made by moving the x-axis slowly and then t would be proportional to x. However, in some embodiments that use confocal imaging, t can be proportional to z.

An optical flow can be determined based on local motion between consecutive 2D images. The optical flow is an observation of the local motion at each area of the image, between two consecutive images in the sequence. The optical flow can be determined by calculating the local motion between the two consecutive images based on a change in position of a point in the two consecutive images and based on a change in time between the two consecutive images. In some embodiments the local motion can be calculated as a 2D motion vector based on a change in position of the point.

For example, given two images at consecutive times, I(t) and I(t+dt), dx and dy can be found such that I(i, j, t)=I(i+dx, j+dy, t+dt). Where vx and vy are components of a 2D velocity and where dx=dt*vx, dy=dt*vy, then I(i, j, t)=I(i+dt*vx, j+dt*vy, t+dt). The components vx and vy can depend upon i, j, and t because the 2D motion vector can vary across the image and vary in time. Using a Taylor expansion: I(i+dt*vx, j+dt*vy, t+dt)=I(i, j, t)+dt*vx*dI/dx+dt*vy*dI/dy+dt*dI/dt=I(x, y, t). Therefore, the optical flow equation can be O(vx, vy, i, j, t)=vx*dI/dx+vy*dI/dy+dI/dt=0.

A motion trajectory 432 of a point in the 3D scan can be estimated. For example, the algorithm can find a motion trajectory that best explains the optical flow of the video sequence given the 3D data. Estimating the motion trajectory can include using a rigid body transformation of the point dependent upon time in the 3D scan. For example, the rigid body transformation can be defined such that applying the rigid body transformation to the point maps the point from a coordinate system at a reference time in the 3D scan to a coordinate system at a recorded time (e.g., time t) of the point in the 3D scan. Non-limiting examples of the reference time can include time 0 (e.g., an initial time of the scan), an end time of the scan, and a middle time of the scan, among other times during the scan. The coordinate system of the scanner is moving along a trajectory T(t), where T(t) is a rigid body transformation that maps (x, y, z) at a recorded time in the scan (e.g., time t) to (x, y, z) at a reference time in the scan (e.g., time 0, an initial time). That is, a point (x, y, z) in the coordinate system of the scanner at time t can be represented as the point T(t)*(x, y, z) in the coordinate system of the scanner at time t=0. A point (x1, y1, z1, t1) can be mapped to the coordinate system at time t0 b applying inverse (T(t0))*T(t1). A goal of motion estimation can be to approximate T(t). Motion compensation 434 can be performed by application of T(t) to points (x, y, z, and t).

Estimating the motion trajectory can include, as an initial guess, estimating a global velocity vector (e.g., (vx, vy) for each consecutive image of the 2D imager I(t), I(t+dt)) based only on the optical flow (e.g., without considering the scan data) and mapping the global velocity vector to a lateral motion trajectory (e.g., T(t)), where the lateral motion trajectory is the estimated motion trajectory. In some embodiments, an position tracking device (e.g., an accelerometer) can be used as an additional input source to provide information to enhance the initial guess. In some embodiments, passive and/or uniform lighting may be assumed for the 2D imager and/or that the 2D imager can be calibrated with respect to the coordinates of the height map.

The estimated motion trajectory can be improved using the optical flow to estimate a correctness of the estimated motion trajectory. For each point (x1, y1, z1, t1) in the scan data, the motion trajectory can be used to find its position in the coordinate system of the scanner at times t, (x(t), y(t), z(t), t). For example, an objective function can be defined that evaluates the correctness of a given motion trajectory according to the optical flow in the video sequence. The 3D data can be used for mapping points to 2D paths in the video sequence. In some embodiments, as an initial guess, an assumption can be made that there is no motion or a simple motion trajectory can be used.

In some embodiments, estimating the correctness of the estimated motion trajectory can include mapping the point from a coordinate system of the 3D scan to a coordinate system of the 2D scan to result in a 2D trajectory for the point. The resulting 2D trajectory (e.g., (i(t), j(t), t)) can de differentiated to determine a number of velocity elements (e.g., vx(t), vy(t)) of the point. The 2D trajectory and the number of velocity elements can be applied to the optical flow (e.g., O(vx(t), vy(t), i(t), j(t), t)=0 for all t). The estimated motion trajectory can be improved by minimizing an objective function that penalizes inaccurate trajectories (e.g., at each point in the 3D scan) based on the optical flow with the applied 2D trajectory and the number of velocity elements. A sum of the squares of the optical flow with the applied 2D trajectory and the number of velocity elements can be calculated between a reference time in the 3D scan and a recorded time of the point in the 3D scan (e.g., O(vx(t), vy(t), i(t), j(t), t) over all points (x1, y1, z1, t1) and all times t). The sum of the squares of the optical flow with the applied 2D trajectory and the number of velocity elements can be minimized to improve the estimated motion trajectory (e.g., Minimize Sum (O(vx(t), vy(t), i(t), j(t), t)^2) over all points (x1, y1, z1, t1) and all times t).

In some embodiments, the 2D trajectory can be regularized to penalize inaccurate trajectories such as unexpected motion patterns, sudden jumps, and/or discontinuities and to stabilize the numerical procedure. The 2D trajectory can be regularized to limit the number of velocity elements within a particular range of velocities. Such a range may be based on a priori knowledge about the motion trajectory that limits it to a reasonable range, penalizes sudden "jumps" between consecutive transformation T(t) and T(t+dt), and/or increases the stability of the numerical procedure. For example, the regularization can be: Minimize Regularization_Term(T(j))+Sum(O(vx(t), vy(t), i(t), j(t), t)^2) over all points (x1, y1, z1, t1) in the scan data over all t.

The improved estimated motion trajectory can be used to compensate for motion during the 3D scan. For example, compensating for motion during the 3D scan can include applying an inverse of the rigid body transformation to the point in the 3D scan to map the point from the recorded time of the point in the 3D scan to the reference time (e.g., time 0, an initial time) in the 3D scan (e.g., time t). That is, given T(t), the 3D scan data can be corrected by applying T(t) to each point (x, y, z, t) to bring each point (x, y, z, t) from the coordinate system of the scanner at time t to the coordinate system of the scanner at time 0.

In various embodiments, motion compensation functionality can be tested using only the 2D imager (e.g., where the 3D scanner is non-functional). A special test object can be prepared for scanning with visible fiducial markings and digitized with the markings. The 2D imager can be calibrated to find the relationship between (x, y, z) coordinates and image coordinates (i, j) in some coordinate system. A sequence of images can be captured while the camera is moved manually over the object. The motion trajectory can be computed from the sequence by, for each image in the sequence, detecting the markings in the image and computing the position of the camera with respect to the object based on the camera calibration. From the motion trajectory, a height map can be calculated, assuming a particular pattern of scanning in the z-direction. From this, the height map and sequence of images can be fed into the previously described algorithm and the results can be tested against the calculated motion trajectory.

Figure 5:
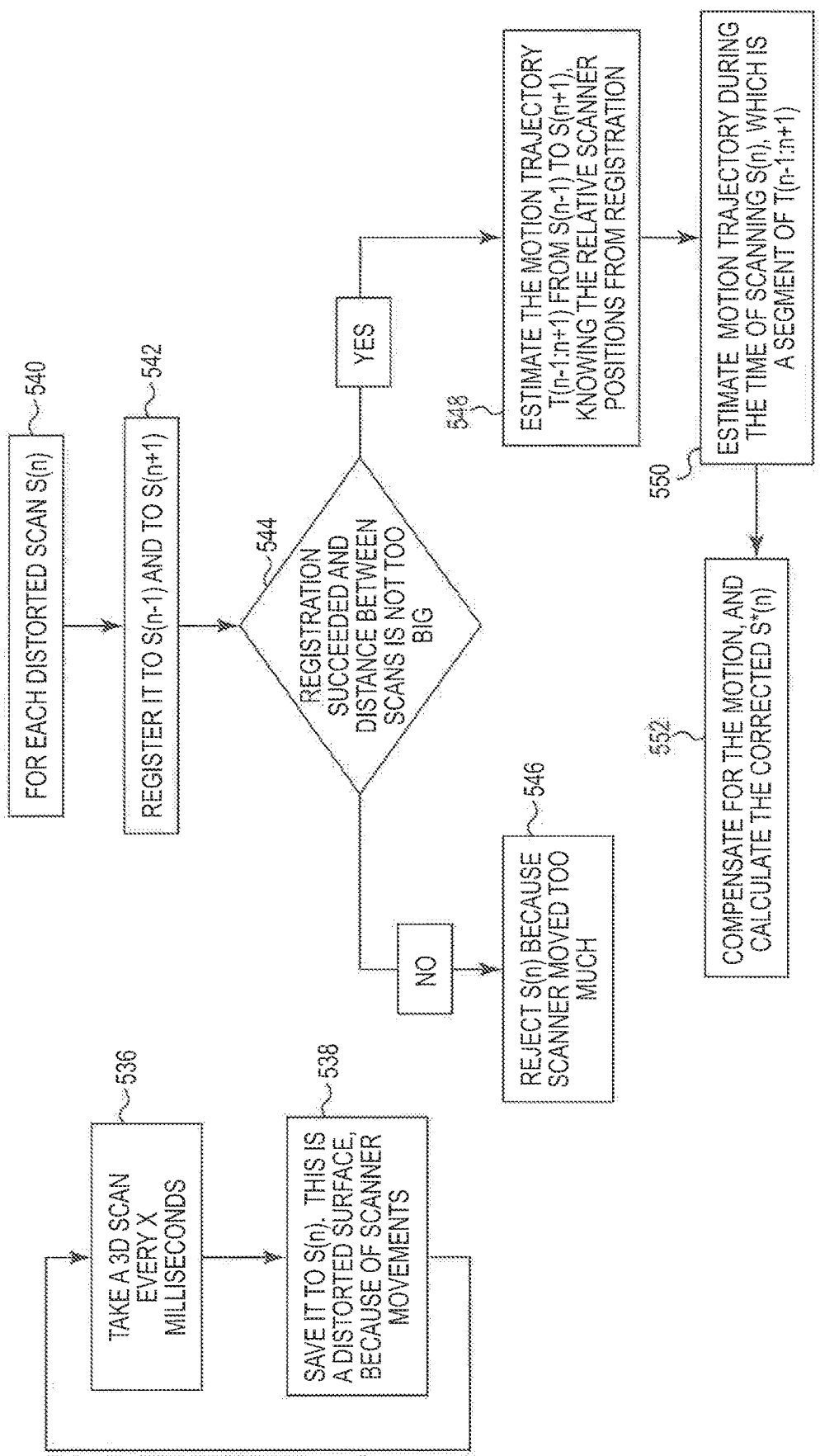
FIG. 5 is a flow chart illustrating a method for motion compensation using 3D data according to a number of embodiments of the present disclosure.

FIG. 5 is a flow chart illustrating a method for motion compensation using 3D data according to a number of embodiments of the present disclosure. Multiple consecutive 3D scans can be used for motion compensation. A sequence of 3D scans 536 can be taken (e.g., at a rate of at least ten 3D scans per second). For example, the 3D scans can be 3D intraoral scans of a patient's dentition. The 3D scans can be saved 538 and distorted scans 540 (e.g., S(n)) can be registered 542 to a previous scan (e.g., an immediately previous scan S(n−1)) and/or to a subsequent scan (e.g., an immediately subsequent scan S(n+1)). In a number of embodiments, a distorted scan can be registered to a plurality of previous 3D scans and/or to a plurality of subsequent 3D scans. In some embodiments, there may be multiple distorted scans (e.g., every scan). Thus, the term "distorted scan" with respect to the description of the use of registration results merely identifies a particular scan that can be used along with a previous scan and a subsequent scan for motion compensation. In various embodiments, a subsequent or previous scan may not be distorted, which can improve correction of the distorted scan by registering it to a scan that is not distorted.

In some embodiments, registration can include aligning the previous scan with respect to the distorted scan and/or aligning the subsequent scan with respect to the distorted scan and determining an overlapping portion of the previous scan with respect to the distorted scan and/or determining an overlapping portion of the subsequent scan with respect to the distorted scan based on the respective alignment. Accuracy of overlap determined based on comparison between surfaces can be dependent on the shape of the object being scanned. For example, an increased number of z-heights that are common to both a first and a second scan can improve the motion estimation that is calculated based at least in part on comparison of scan surfaces.

Aligning two different scans can include the use of a rigid body transformation (e.g., R(n−1:n)) on the previous scan (e.g., S(n−1)) to align it with the distorted scan (e.g., S(n)) and/or a rigid body transformation (e.g., R(n+1:n)) on the subsequent scan (e.g., S(n+1)) to align it with the distorted scan (e.g., S(n)). The rigid body transformation is a six degrees of freedom transformation. An amount of movement can be determined between the previous scan and the distorted scan and/or between the distorted scan and the subsequent scan based on the respective overlapping portion and/or based on the respective non-overlapping portion.

A determination 544 can be made as to whether an amount of movement between the previous scan, the distorted scan, and the subsequent scan (e.g., based on the respective overlapping portion and/or based on the respective non-overlapping portion) is within a registration threshold. If the amount of movement is not within the threshold (e.g., if the scanner moved too much during the scan), then the distorted scan can be rejected 546. If the amount of movement is within the registration threshold, then a first motion trajectory 548 can be estimated from the previous scan to the subsequent scan based on the registration (e.g., T(n−1:n+1) from S(n−1) to S(n+1)). The registration can be used to provide knowledge of the relative positions during the previous, distorted, and subsequent scans.

The registration results can signify snapshots of the trajectory T(t . . . i) at a finite number of times (t . . . i) and the motion trajectory can be computed from those snapshots by an interpolation method. The number of points (t . . . i) and the interpolation may vary. In some embodiments the first motion trajectory can be a snapshot of an overall motion trajectory across a plurality of 3D scans. The overall motion trajectory can be calculated based on a plurality of snapshots each associated with a respective registered one of the plurality of 3D scans.

A second motion trajectory 550 can be estimated during a scanning time of the distorted scan. The second motion trajectory can be a segment of the first motion trajectory (e.g., T(n−1:n+1)) during S(n). The second motion trajectory can be estimated in response to the amount of movement being within the registration threshold.

In some embodiments, registration can include associating a first point on a time axis in a middle of a scanning time of a previous scan with a rigid body transformation of the previous scan that aligns the previous scan with the distorted scan. A second point on the time axis in a middle of a scanning time of the subsequent scan can be associated with a rigid body transformation of the subsequent scan that aligns the subsequent scan with the distorted scan. Estimating the first motion trajectory can include interpolating between the first rigid body transformation and the second rigid body transformation. Estimating the second motion trajectory can include trimming the first motion trajectory to only include motion trajectory during the scanning time of the distorted scan.

A corrected scan 552 (e.g., S*(n)) can be calculated for the distorted scan by compensating for the motion trajectory during the scanning time of the distorted scan. The scan can be corrected in response to the amount of movement being within the registration threshold. Thus, in some embodiments, using registration, motion compensation can be performed without the use of extra data for motion estimation (e.g., position tracking devices and/or a 2D imager). However, such extra data can be included to further improve motion compensation as described herein. In various embodiments, the registration of the distorted scan, estimation of the first motion trajectory, estimation of the second motion trajectory, and calculation of the corrected scan can be iteratively repeated to improve an accuracy of the corrected scan. Iterative repetition can improve an accuracy of the scans. After correcting for distortion, the registration itself can become more accurate, which can improve the next iterative correction. The iterative repetition can continue until the results converge, for example.

Figure 6:
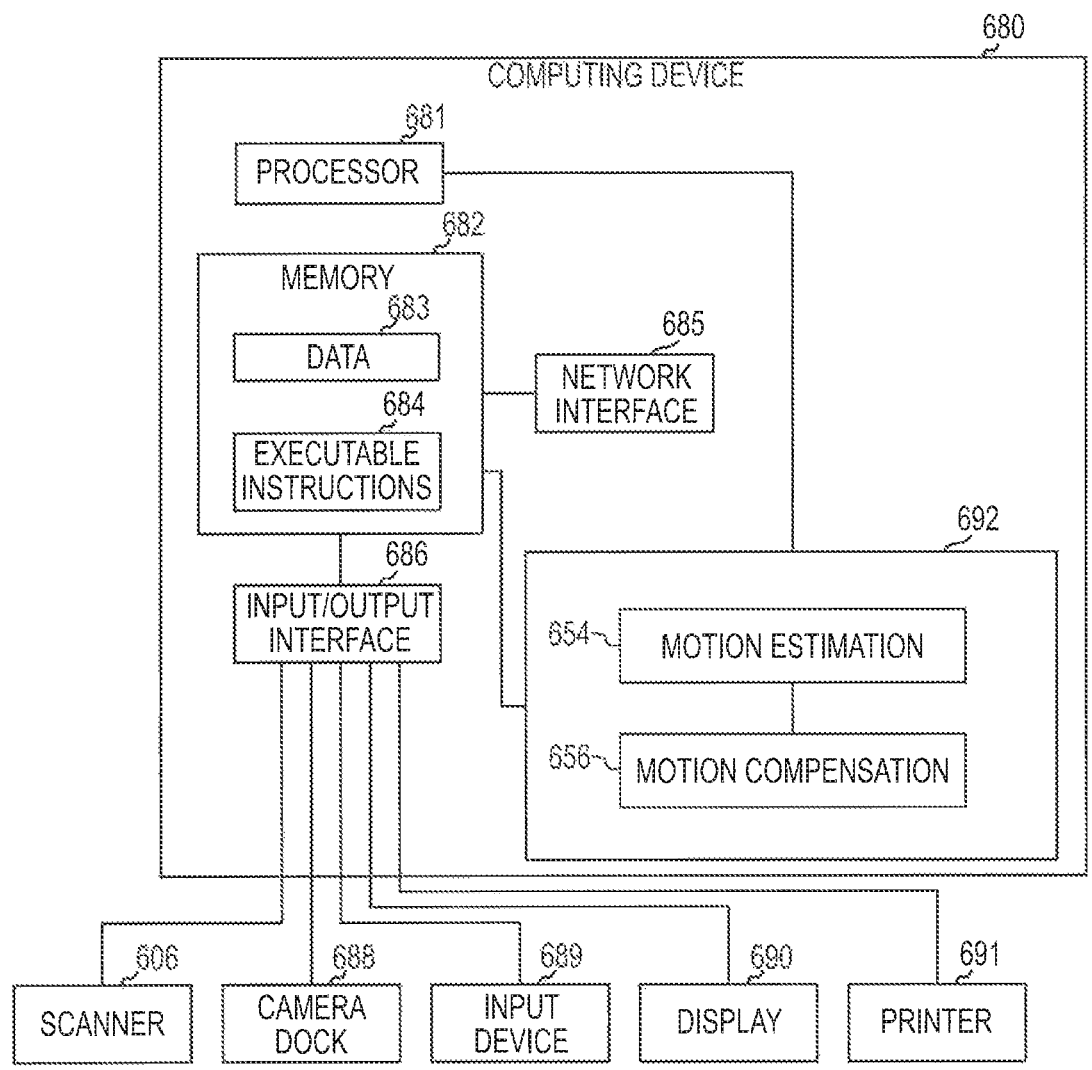
FIG. 6 illustrates a system for motion compensation in a 3D scan according to a number of embodiments of the present disclosure.

FIG. 6 illustrates a system for motion compensation in a 3D scan according to a number of embodiments of the present disclosure. The system illustrated in FIG. 6 can include a computing device 680 having a number of components coupled thereto. The computing device 680 can include a processing module 681 (e.g., one or more processors) and memory 682. The memory 682 can include various types of information including data 683 and executable instructions 684 as discussed herein. The memory 682 can be a tangible non-transitory computer readable medium having instructions 684 that can be executed by the processing module 681 to cause the computing device 680 to perform various functions as described herein.

The memory 682 and/or the processing module 681 may be located on the computing device 680 or off the device in some embodiments. As such, as illustrated in the embodiment of FIG. 6, a system can include a network interface 685. Such an interface can allow for processing on another networked computing device or such devices can be used to obtain information about the patient or executable instructions for use with various embodiments provided herein.

As illustrated in the embodiment of FIG. 6, a system can include one or more input and/or output interfaces 686. Such interfaces can be used to connect the computing device 680 with one or more input or output devices.

For example, in the embodiment illustrated in FIG. 6, the system includes connectivity to a scanning module 606 (e.g., an intraoral scanner including one or more of a 3D scanner, a 2D imager, and/or a number of position tracking devices as described herein), a camera dock 688, an input device 689 (e.g., a keyboard, mouse, etc.), a display device 690 (e.g., a monitor), and a printer 691. The input/output interface 686 can receive data, storable in the data storage device (e.g., memory 682), representing 3D and/or 2D data, among other data, corresponding to the patient's dentition. Although the scanning module 606 is illustrated as a component separate from the computing device 680, in some embodiments, the scanning module 606 (e.g., the intraoral scanner) can include the components and/or functionality described herein with respect to the computing device 680 (e.g., the scanning module 606 can perform motion detection and/or motion compensation).

In some embodiments, the scanning module 606 can be configured to scan a physical mold of a patient's upper jaw and a physical mold of a patient's lower jaw. In one or more embodiments, the scanning module 606 can be configured to scan the patient's upper and/or lower jaws directly (e.g., intraorally).

The camera dock 688 can receive an input from an imaging device (e.g., a 2D imaging device) such as a digital camera or a printed photograph scanner separate from any 2D imaging device on the scanning module 606. The input from the imaging device can be stored in the data storage device 682.

The processing module 681 can be configured to provide a visual indication of a virtual dental model on the display 690 (e.g., on a GUI running on the processing module 681 and visible on the display 690). The processing module 681 can further be configured (e.g., via computer executable instructions stored in a tangible non-transitory computer readable medium) to perform the various methods, algorithms, and/or functionality described herein. The processing module 681, in association with the data storage device 682, can be associated with data and/or application modules 692. The processing module 681, in association with the data storage device 682, can store and/or utilize data and/or execute instructions to provide a number of application modules for motion compensation in a 3D scan.

Such connectivity can allow for the input and/or output of virtual dental model information or instructions (e.g., input via keyboard) among other types of information. Although some embodiments may be distributed among various computing devices within one or more networks, such systems as illustrated in FIG. 6 can be beneficial in allowing for the capture, calculation, and/or analysis of information discussed herein.

A system for motion compensation can include a scanning module 606 and a processing module 681). The scanning module 606 can include an intraoral 3D scanner and, in some embodiments, at least one position tracking device coupled to the 3D scanner. Position tracking devices can include one or more of an accelerometer (e.g., to measure acceleration of the 3D scanner), a gyroscope (e.g., to measure angular velocity of the 3D scanner), among others. Other position tracking devices can include the use of triangulation, trilateration, or multilateration to determine position, for example using Wi-Fi, Bluetooth, or other wireless systems.

The processing module 681 can (e.g., via application module 692) receive a plurality of 3D scans of a dentition and estimate a motion trajectory from a particular one of the plurality of scans to a subsequent scan. The estimation can include one or more of registering the particular scan to at least one of a previous scan and the subsequent scan, determining whether an amount of movement between the previous scan, the particular scan, and the subsequent scan is within a registration threshold, and estimating the motion trajectory based on the registration, using data from a plurality of two-dimensional (2D) images of the dentition taken during the particular scan of the dentition, determining an optical flow based on local motion between consecutive images of the plurality of 2D images, estimating a motion trajectory of a point in the particular scan, improving the estimated motion trajectory using the optical flow to estimate a correctness of the estimated motion trajectory, and estimating 654 an amount of motion of the 3D scanner during a 3D scan as a rigid body transformation based on input from the at least one position tracking device. The processing module 681 (e.g., via application module 692) can calculate a corrected scan by compensating for the motion trajectory according to any of the techniques described herein.

The processing module 681 can estimate the motion trajectory and calculate the corrected scan in response to the amount of movement being within the registration threshold, and to reject the particular scan in response to the amount of movement being outside of the registration threshold. The processing module 681 can register the particular scan to a plurality of previous scans and to a plurality of subsequent scans.

The processing module 681 can align the previous scan with respect to the particular scan, determine an overlapping portion of the previous scan with respect to the particular scan based on the alignment, and determine an amount of movement between the previous scan and the particular scan based on the overlapping portion and/or a non-overlapping portion to register the particular scan to the at least one of the previous scan and the subsequent scan. The motion trajectory can be a snapshot of an overall motion trajectory across the plurality of scans, and where the instructions can be executed by the processor to compute the overall motion trajectory based on a plurality of snapshots each associated with a respective registered one of the plurality of scans.

The at least one position tracking device can be coupled to the 3D scanner and the processing module 681 can be configured to compensate 656 for the estimated amount of motion by applying an inverse of the rigid body transformation to a plurality of points comprising the particular scan. A 2D imager can be coupled to the 3D scanner and the processing module 681 can estimate a velocity of the 3D scanner based on input from the at least one position tracking device and to reset the estimated velocity to zero in response to input from the 2D imager indicating that the 3D scanner is not moving. The processing module 681 can reset the estimated velocity to zero in six degrees of freedom in response to the input from the 2D imager comprising the plurality of 2D images indicating that the 3D scanner is not moving.

The 3D scanner can be in a first reference frame and the scanning module 606 can include a 2D imager in a second reference frame that is fixed with respect to the first reference frame. The processing module 681 can receive the data from the plurality of 2D images of the dentition taken, with the 2D imager, during a particular scan of the dentition, where each of the plurality of 2D images is associated with a respective time in the particular scan. The processing module 681 can compensate for motion during the scan using the improved estimated motion trajectory.

The processing module 681 can calculate the local motion between two consecutive images based on a change in position of a point in the two consecutive images and based on a change in time between the two consecutive images to determine the optical flow. The processing module 681 can estimate a global velocity vector based only on the optical flow. The processing module can map the global velocity vector to a lateral motion trajectory comprising the estimated motion trajectory.

The processing module 681 can map the point from a coordinate system of the scan to a coordinate system of the image to result in a 2D trajectory for the point. The processing module 681 can differentiate the resulting 2D trajectory to determine a number of velocity elements of the point. The processing module 681 can apply the 2D trajectory and the number of velocity elements to the optical flow. The processing module can sum squares of the optical flow with the applied 2D trajectory and the number of velocity elements between a reference time in the scan and a recorded time of the point in the scan to estimate the correctness of the estimated motion trajectory.

The processing module 681 can minimize an objective function that penalizes inaccurate trajectories at each point in the scan based on the optical flow with the applied 2D trajectory and the number of velocity elements to improve the estimated motion trajectory. The processing module 681 can regularize the 2D trajectory to penalize inaccurate trajectories.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

It will be understood that when an element is referred to as being "on," "connected to" or "coupled with" another element, it can be directly on, connected, or coupled with the other element or intervening elements may be present. In contrast, when an element is referred to as being "directly on," "directly connected to" or "directly coupled with" another element, there are no intervening elements or layers present. As used herein, the term "and/or" includes any and all combinations of one or more of the associated listed items.

It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A system, comprising:
   a non-transitory memory having computer-readable instructions for compensating for motion in a three-dimensional (3D) scan using two-dimensional (2D) images collected during the 3D scan; and
   a processor coupled to the non-transitory memory and configured to execute the computer-readable instructions to:
   receiving a plurality of 3D scans taken of a dentition using a 3D scanner, the 3D scanner including a position tracking device and a two-dimensional (2D) imager;
   estimating a velocity of the 3D scanner during the 3D scan using a rigid body transformation based on input from the position tracking device in response to input from the 2D imager; and
   compensating for motion during the 3D scan based on the estimated velocity from the position tracking device.

2. The system of claim 1, wherein estimating the velocity of the 3D scanner comprises estimating the velocity is in six degrees of freedom in response to the input from the 2D imager.

3. The system of claim 1, wherein the 2D imager collects a plurality of 2D images taken during the 3D scan.

4. The system of claim 1, wherein estimating the velocity of the 3D scanner comprises:
   aligning a previous scan or a subsequent scan of the plurality of 3D scans with a distorted scan of the plurality of 3D scans, and determining an overlap based on the alignment; and
   aligning the previous scan or the subsequent scan with the distorted scan by the rigid body transformation.

5. The system of claim 1, wherein compensating for the motion during the 3D scan comprises applying the rigid body transformation.

6. The system of claim 1, wherein the rigid body transformation is applied to each point of a particular 3D scan to bring each point from a coordinate system of the 3D scanner at recorded time to a coordinate system of the 3D scanner at a reference time.

7. The system of claim 1, further comprising instructions to estimate an amount of motion of a 3D scanner based on input from at least one position tracking device.

8. A computer implemented method for compensating for motion in three-dimensional (3D) scanning of a dentition, comprising:
   receiving a plurality of 3D scans taken of the dentition using a 3D scanner, the 3D scanner including a position tracking device and a two-dimensional (2D) imager;
   estimating a velocity of the 3D scanner during the 3D scan using a rigid body transformation based on input from the position tracking device in response to input from the 2D imager; and
   compensating for motion during the 3D scan based on the estimated velocity from the position tracking device.

9. The method of claim 8, wherein estimating the velocity of the 3D scanner comprises estimating the velocity is in six degrees of freedom in response to the input from the 2D imager.

10. The method of claim 8, wherein the 2D imager collects a plurality of 2D images taken during the 3D scan.

11. The method of claim 8, wherein estimating the velocity of the 3D scanner comprises:
    aligning a previous scan or a subsequent scan of the plurality of 3D scans with a distorted scan of the plurality of 3D scans, and determining an overlap based on the alignment; and
    aligning the previous scan or the subsequent scan with the distorted scan by the rigid body transformation.

12. The method of claim 8, wherein compensating for the motion during the 3D scan comprises applying the rigid body transformation.

13. The method of claim 8, wherein the rigid body transformation is applied to each point of a particular 3D scan to bring each point from a coordinate system of the 3D scanner at recorded time to a coordinate system of the 3D scanner at a reference time.

14. The method of claim 8, further comprising estimating an amount of motion of the 3D scanner based on input from the position tracking device.

15. A dental scanning system, comprising:
   a three-dimensional (3D) scanner configured to collect 3D scans of a patient's dentition, the 3D scanner including a two-dimensional (2D) imager configured to collect 2D images during collection of the 3D scans;
   a processor configured to execute computer-readable instructions for:
      receiving a plurality of 3D scans taken of the patient's dentition using a 3D scanner, the 3D scanner including a position tracking device and the 2D imager;
      estimating a velocity of the 3D scanner during the 3D scan using a rigid body transformation based on input from the position tracking device in response to input from the 2D imager; and
      compensating for motion during the 3D scan based on the estimated velocity from the position tracking device.

16. The dental scanning system of claim 15, wherein estimating the velocity of the 3D scanner comprises estimating the velocity is in six degrees of freedom in response to the input from the 2D imager.

17. The dental scanning system of claim 15, wherein the 2D imager collects a plurality of 2D images taken during the 3D scan.

18. The dental scanning system of claim 15, estimating the velocity of the 3D scanner comprises:
   aligning a previous scan or a subsequent scan of the plurality of 3D scans with a distorted scan of the plurality of 3D scans, and determining an overlap based on the alignment; and
   aligning the previous scan or the subsequent scan with the distorted scan by the rigid body transformation.

19. The dental scanning system of claim 15, wherein compensating for the motion during the 3D scan comprises applying the rigid body transformation.

20. The dental scanning system of claim 15, wherein the rigid body transformation is applied to each point of a particular 3D scan to bring each point from a coordinate system of the 3D scanner at recorded time to a coordinate system of the 3D scanner at a reference time.

21. The dental scanning system of claim 15, further comprising estimating an amount of motion of a 3D scanner based on input from at least one position tracking device.

\* \* \* \* \*